United States Patent [19]
Liskow et al.

[11] Patent Number: 5,847,832
[45] Date of Patent: Dec. 8, 1998

[54] MOIRÉ TOPOGRAPHIC MEASUREMENT

[75] Inventors: Dean H. S. Liskow; James P. Kelly; Joseph N. Paranto; Felix E. Morgan, all of Albuquerque, N. Mex.

[73] Assignees: Hughes Aircraft Company, Goleta, Calif.; University of New Mexico, Albuquerque, N. Mex.

[21] Appl. No.: 616,898

[22] Filed: Mar. 15, 1996

[51] Int. Cl.$^6$ .................................................. G01B 11/24
[52] U.S. Cl. ......................... 356/376; 356/374; 356/378
[58] Field of Search .................. 356/376, 374, 356/378

[56] References Cited

U.S. PATENT DOCUMENTS

| | | | |
|---|---|---|---|
| 3,728,998 | 4/1973 | Heine | 128/9 |
| 3,874,371 | 4/1975 | Stadler et al. | 128/9 |
| 3,934,578 | 1/1976 | Heine | 128/9 |
| 3,978,850 | 9/1976 | Moore et al. | 128/9 |
| 4,147,163 | 4/1979 | Newman et al. | 128/9 |
| 4,335,713 | 6/1982 | Komiya | 128/9 |
| 4,374,526 | 2/1983 | Kemp | 128/9 |
| 4,434,800 | 3/1984 | Anson et al. | 128/665 |
| 4,564,295 | 1/1986 | Halioua | 356/376 |
| 4,567,881 | 2/1986 | Heller | 126/440 |
| 4,652,093 | 3/1987 | Stephen et al. | 350/500 |
| 4,692,003 | 9/1987 | Adachi et al. | 351/212 |
| 4,794,550 | 12/1988 | Greivenkamp, Jr. | 364/562 |
| 4,854,708 | 8/1989 | Kafri et al. | 356/359 |
| 4,884,447 | 12/1989 | Kemp et al. | 73/585 |
| 4,913,132 | 4/1990 | Gabriel | 128/9 |
| 4,986,262 | 1/1991 | Saito | 128/6 |
| 5,016,173 | 5/1991 | Kenet et al. | 364/413.13 |
| 5,038,755 | 8/1991 | Burgio et al. | 128/9 |
| 5,080,477 | 1/1992 | Adachi | 351/212 |
| 5,090,400 | 2/1992 | Saito | 128/6 |
| 5,098,426 | 3/1992 | Sklar et al. | 606/5 |

(List continued on next page.)

OTHER PUBLICATIONS

Cline, Harvey E., William E. Lorensen and Andrew S. Holik, "Automatic Moire Contouring," *Applied Optics*, vol. 23, No. 10 (15 May 1984), pp. 1454–1459.

American Academy of Otolaryngology—Head and Neck Surgery Report: "*Infant Hearing Evaluation,*" Joint Committe on Infant Hearing 1994 Position Statement.

Arlinger, Stig D., "Normal Hearing Threshold Levels in the Low–frequency Range Determined by an Inser Earphone," *Journal of the Acoustic Society of America* vol. 90 No. 5 (Nov. 1991), pp. 2411–2414.

(List continued on next page.)

*Primary Examiner*—Frank G. Font
*Assistant Examiner*—Reginald A. Ratliff
*Attorney, Agent, or Firm*—Deborah A. Peacock; Rod D. Baker; Jeffrey D. Myers

[57] ABSTRACT

A hand-held instrument (10) and associated method for providing optical measurements of the contour, range and motion of an object, such as a tympanic membrane of an ear, in real time, and to provide for simultaneous visualization of the object. The instrument (10) includes an illumination source (22) that projects an optical beam (24) through a grating (26) onto a gradient of refractive index lens (32) to project light and dark fringes onto the object at stepped phases determined by the grating position. Light reflected from the object is collected and focused onto an eye piece (18) to be observed by the operator. Simultaneously, reflected light from the object is focused onto a camera (46). The camera (46) generates an electrical signal in proportion to the light intensity received by the camera (46) to generate an image of the object. The image is then transmitted to processing systems to compute phase relationships in the reflected grating image to generate a contour map of the object. A drive system (28) is provided to move the grating (26) to different positions at a fraction of the spatial period of the grating during a measurement to provide phase sensitivity, eliminate reflectivity variations and reduce background noise.

109 Claims, 4 Drawing Sheets

U.S. PATENT DOCUMENTS

| | | | |
|---|---|---|---|
| 5,159,361 | 10/1992 | Cambier et al. | 351/212 |
| 5,239,984 | 8/1993 | Cane et al. | 128/9 |
| 5,307,151 | 4/1994 | Hof et al. | 356/376 |
| 5,307,152 | 4/1994 | Boehlein et al. | 356/376 |
| 5,363,839 | 11/1994 | Lankford | 128/9 |
| 5,379,107 | 1/1995 | Hannssen et al. | 356/376 |
| 5,473,392 | 12/1995 | Klopotek | 351/205 |
| 5,479,221 | 12/1995 | Heine et al. | 351/214 |

OTHER PUBLICATIONS

Bone, Donald J., H. –A.Bachor, and R. John Sandeman, "Fringe–Pattern Analysis Using a 2–D Fourier Transform," *Applied Optics*, vol. 25 No. 10 (May 15, 1986), pp. 1653–1660.

Clarke, John, "SQUIDs" (Superconducting Quantum Interference Devices), *Scientific American* (Aug. 1994), pp. 46–53.

Daly, Kathleen A., "Epidemiology of Otitis Media," *Otolaryngologic Clinics of North America* vol. 24, No. 4, (Aug. 1991) pp. 775–786.

Decraemar, Willem F., Joris J.J.Dirckx, and W. Robert J.Funnell, "Shape and Derived Geometrical Parameteres of the Adult, Human Tympanic Membrane Measured with a Phase–Shift Moiré Interferometer," *Hearing Research*, vol. 51 (1991), pp. 107–122.

Deng, Kung–Li and Jyhpyng Wang, "Nanometer–Resolution Distance Measurement with a Noninterferometric Method," *Applied Optics*, vol. 33 No. 1 (Jan. 1, 1994), pp. 113–116.

Dirckx, J.J.J. and W.F. Decraemer, "Human Tympanic Membrane Deformation Under Static Pressure," *Hearing Research*, vol. 51 (1991), pp. 93–106.

Dirckx, J.J.J. and W.F. Decraemer, "Automatic Calibration Method for Phase Shift Shadow Moiré Interferometry," *Applied Optics*, vol. 29 No. 10, (Apr. 1, 1990), pp. 1474–1476.

Dirckx, J.J.J., W.F. Decraemer and G. Dielis, "Phase Shift Method Based on Object Translation for Full Field Automatic 3–D Surface Reconstruction from Moiré Topograms," *Applied Optics*, vol. 27 No. 6, (Mar. 15, 1988), pp. 1164–1169.

Goode, R. L., G. Ball and S. Nishihara, "Measurement of Umbo Vibration in Human Subjects—Method and Possible Clinical Applications," *American Journal of Otolaryngology*, vol. 14, (1993), pp. 247–251.

Goycoolea, Marcos V., Marcelo M. Hueb and Carlos Ruah, "Definitions and Terminology," *Otolaryngologic Clinics of North America* vol. 24, No. 4, (Aug. 1991), pp. 757–761.

Hardy, John W., "Adaptive Optics," *Scientific American*, (Jun. 1994), pp. 60–65.

Idesawa, Masanori, Toyohiko Yatahai and Takashi Soma, "Scanning Moiré Method and Automatic Measurement of 3–D Shapes," *Applied Optics* vol. 16 No. 8 (Aug. 1977), pp. 2152–2162.

Jacobs, Laurence J. and Craig A. Woolsey, "Transfer Functions for Acoustic Emissions Transducers Using Laser Interferometry," *Journal of the Acoustical Society of America* vol. 94 No. 6 (Dec. 1993), pp. 3506–3508.

Kempthorne, Jill and G. Scott Giebink, "Pediatric Approach to the Diagnosis and Management of Otitis Media," *Otolaryngologic Clinics of North America* vol. 24, No. 4, (Aug. 1991), pp. 905–929.

Klienman, Lawrence C., Jacqueline Kosecoff, Robert W.Dubois and Robert H.Brook, "The Medical Appropriateness of Tympanostomy Tubes Proposed for Children Younger than 16 Years in the United States," *Journal of the American Medical Asssociation* vol. 271 No. 16 (Apr. 27, 1994), pp. 1250–1255.

Konrádson, K.S., A. Ivarsson and S. Harris, "Three–dimensional laser Doppler Interferometric Display of Human Tympanic Membrane Vibrations at Two Different Frequencies and Sound Pressure Levels," *Acta Otolaryngol* vol. 449 (1988), pp. 183–186.

Lichtman, Jeff W., "Confocal Microscopy," *Scientific American*, (Aug. 1994), pp. 40–45.

Lindberg, Sven and Thomas Runer, "Method for In Vivo Measurement of Mucociliary Activity in the Human Nose," *Ann Otol Rhinol Laryngol* vol. 103 (1994), pp. 558–566.

Løkberg, O.J., K. Høgmoen and T. Gundersen, "Vibration Measurement of the Human Tympanic Membrane–In Vivo," *Acta Otolaryngol* vol. 89, (1980), pp. 37–42.

Margolis, Robert H. and Lisa L. Hunter, "Audiologic Evaluation of the Otitis Media Patient," *Otolaryngologic Clinics of North America* vol. 24, No. 4, (Aug. 1991), pp. 877–899.

Meadows, D. M., W.O. Johnson and J.B. Allen, "Generation of Surface Contours by Moiré Patterns," *Applied Optics* vol. 9, (1970), pp. 942–947.

Poe, Dennis S.,Elie E. Rebeiz,Michail M. Pankratov, Stanley M. Shapshay, "Transtympanic Endoscopy of the Middle Ear," *Laryngoscope* vol. 102, Sep. 1992), pp. 993–996.

Stasche, N., H. Foth, K. Hörmann, A. Baker and C. Hutoff, "Middle Ear Transmission Disorder—Typanic Membrane Vibration Analysis by Laser–Doppler–Vibrometry," *Acta Otolaryngol* vol. 114, (1994), pp. 59–63.

Takajo, Hiroaki and Takahasji, Tohru, "Noniterative Method for Obtaining the Exact Solution for the Normal Equation in Least–Squares Phase Estimation from the Phase Difference," *Journal of the Optical Society of America*, vol. 5 No. 11, (Nov. 1988), p. 1818.

Takasaki, H., "Moiré Topography," *Applied Optics*, vol. 9, No. 6, (Jun., 1970), pp. 1467–1472.

Takeda, Mitsuo, Hideki Ina and Seihi Kobayashi, "Fourier–Transform Method of Fringe–Pattern Analysis for Computer–based Topography and Interferometry," *Journal of the Optical Society of America* vol. 72 No. 1, (Jan. 1982), pp. 156–160.

Takeda, Mitsuo, et al., "Fourier Transform Profilometry for the Automatic Measurement of 3–D Object Shapes," *Applied Optics*, vol. 22 No. 24, (Dec. 15, 1983), pp. 3977–3982.

"Video–Electronic Generation of Real Time Moiré Topograms," H. Kugel and F. Lanzl, Institut für Angewandte Physik, Universitaät Hamburg, undated.

von Unge, M., W.F. Decraemer, D. Bagger–Sjöbäck and J.J. Dirckx, "Displacement of the Gerbil Tympanic Membrane Under Static Pressure Variations Measured with a real–time differential Moiré Interferometer," *Hearing Research* vol. 70, (1993), pp. 229–242.

Voss, Susan E. and Jont B. Allen, "Measurement of Acoustic Impedance and Reflectance in the Human Ear Canal," *Journal of the Acoustical Society of America* vol. 95 No. 1 (Jan. 1994), pp. 372–384.

Werkhaven, J.A., L. Reinisch, M. Sorrell, J. Tribble, and R.H. Ossoff, "Noninvasive Optical Diagnosis of Bacteria Causing Otitis Media," *Laryngoscope* vol. 104 (Mar. 1994), pp. 264–268.

MOIRÉ TOPOGRAPHIC MEASUREMENT

BACKGROUND OF THE INVENTION

1. Field of the Invention

This invention relates generally to a method and apparatus for making measurements of an object and, more particularly, to a method and apparatus for measuring the contour, shape, surface, range and motion of fairly inaccessible living membranes or tissues utilizing moiré topography and gradient of refractive index optics. This invention further relates generally to a hand-held medical instrument for making non-invasive examinations of living membranes or tissues and, more particularly, to a hand-held otoscope that incorporates a projection moire topography system and gradient of refractive index optics for making a non-invasive examination and storing data about the surface topography and other properties of the tympanic membrane of the ear.

2. Discussion of the Related Art

Otitis Media or inflammation of the middle ear, caused by bacterial infection, affects a large number of people, especially children under seven years of age. At the present time, physicians rely principally on a conventional otoscope, developed during the 19th century, to make an initial diagnosis in a patient who complains of pain within the middle ear and may be afflicted with otitis media. In its simplest form, the conventional otoscope consists of an eye piece, a magnifying lens, a light source and a speculum all mounted on an otoscope body containing a battery power supply. Light emitted by the light source is reflected off of the tympanic membrane, a semi-transparent tissue barrier between the middle ear and the external ear canal, and is magnified by the lens to enable the physician to view the tympanic membrane through the eye piece. An example of a conventional otoscope can be found in U.S. Pat. No. 4,643,171 issued to Riester Feb. 17, 1987.

During examination with an otoscope, the physician inserts the speculum of the otoscope into the external ear canal of the patient to examine visually the patient's tympanic membrane through the eye piece. During this examination, the physician gathers an impression of the shape of the tympanic membrane, in particular any displacement caused by fluid accumulation in the middle ear, evaluates the color of the tympanic membrane, in particular redness associated with dilation of blood vessels of the tympanic membrane and middle ear, and searches for perforations of the tympanic membrane and leakage of fluid into the external ear canal. In addition, the physician may evaluate the mobility of the tympanic membrane by squeezing a pneumatic bulb associated with the otoscope to change the pressure in the external ear canal. The extent to which the tympanic membrane moves in response to this transient pressure change is then observed. During the examination, the physician may make handwritten notes about the condition of the patient's ear, as viewed with the otoscope, to document the examination as part of the patient's medical record. Conventional otoscopy therefore involves purely subjective and qualitative evaluation of the patient's ear.

If the physician finds an indication of infection or other potential problems, a particular course of therapy may be recommended. Additional diagnostic tests may also be required including tympanometry. Tympanometry involves the use of a tympanometer that measures the acoustic impedance of the entire tympanic membrane to detect the existence of perforations in the tympanic membrane or abnormal negative pressure in the middle ear associated with infection. Such a procedure is carried out by an audiologist.

If the diagnosis is an infection of the middle ear, antibiotics are commonly prescribed for the patient. In many cases, however, antibiotics are prescribed when the diagnosis of an ear infection is questionable. It is likely that the use of antibiotics without clear evidence of bacterial infection contributes to the growing world-wide problem of antibiotic resistant microorganisms. Quantitative evidence for the presence of bacterial infection would be a significant advance in diagnosis of middle ear disease.

Patients who have persistent middle ear problems are generally surgically treated by a specialist in otolaryngology. The specialist may implant pressure equalization tubes in the tympanic membrane of the patient to drain fluid from the middle ear space. The placement of pressure equalization tubes has been questioned by the insurance industry and by the medical profession because uniform objective criteria for the placement of tubes have not been established, and a significant percentage of tube placements may be unwarranted.

Analysis of current modes of practice in otoscopy suggest a need for improvements in the diagnosis of ear disease in a number of areas. These areas include static and dynamic quantitative measurements of the properties of the tympanic membrane, and record storage of the quantitative measurements. For examples of static measurements, the patient's ear should be evaluated with a non-invasive method that permits rapid collection of quantitative information on the characteristics of the tympanic membrane. A three-dimensional (3D) (usually height, width, and depth) image of the surface of the tympanic membrane should be provided to detect displacements produced by either negative or positive pressure in the middle ear, bulges produced by tumors or fluid accumulating in the middle ear space, and the sizes and locations of perforations in the tympanic membrane. Also, the color of the tympanic membrane, which reddens as blood vessels dilate in response to infection, should also be measured. For dynamic measurements, a visual display of the displacement of the tympanic membrane in response to calibrated changes in external ear canal pressure should be provided. This is equivalent to a two-dimensional display of the compliance of the tympanic membrane to establish local changes in the mobility of the tympanic membrane that could provide information about the underlying cause of any change in mobility. Data and images of the tympanic membrane should be stored on magnetic media to replace handwritten notes and supplant subjective impressions as the basis for diagnosis. The stored information would allow the physician to track the patient's condition from visit to visit, produce documentation for the choice of therapy, and be compatible with electronic data transmission for expert consultation at remote sites.

What is needed then is a modern medical instrument for a practical clinical environment that allows for real time static and dynamic observations of a relatively inaccessible living membrane, such as a tympanic membrane, and provides simultaneous record storage of the observations and visualization of the membrane by a physician.

A moiré pattern results when at least two geometrically regular patterns are superimposed on each other. By moving one of the patterns relative to the other, it has been shown that accurate measurements of minute displacements can be measured by analysis of the resulting moiré pattern. Projection moiré topography is a contour measurement technique using a grating to produce a moiré pattern that has been shown to be applicable to measure the topographical contours of inanimate objects and living membranes. For discussions of projection moiré topography of this type, see for example, Takasaki, H., "Moiré Topography", APPLIED OPTICS, Vol. 9, No. 6, June 1970, pp. 1467–1472; Takasaki, Hiroshi, "Moiré Topography from its Birth to Practical Application," OPTICS AND LASERS IN ENGINEERING, 3 (1982) pp. 3–14; Dirckx, J. J. J., et al., "Phase Shift Method Based on Object Translation for Full Field Automatic 3-D Surface Reconstruction from Moiré Topograms," APPLIED OPTICS, Vol. 27, No. 6, Mar. 15, 1988, pp. 1164–1169, Dirckx, J. J. J., et al., "Automatic Calibration Method for Phase Shift Shadow Moiré Interferometry," APPLIED OPTICS, Vol. 29, No. 10, Apr. 1, 1990, pp. 1474–1476; and Takeda, Mitsuo et al., "Fourier Transform Profilometry for the Automatic Measurement of 3-D Object Shapes," APPLIED OPTICS, Vol. 22, No. 24, Dec. 15, 1983, pp. 3977–3982.

In one type of projection moiré topography, a light source is used to project an image of a grating onto an object whose shape is to be measured to form light and dark fringes on the object. A grating drive system moves the grating a small amount in the plane of the grating to three phase stepped positions relative to the period of the grating lines. Phase-stepped images of the grating are reflected off of the object, and are captured by an optical sensor along a different optical axes to produce parallax in the sensed image. The position of the reflected images of the grating at each position are distorted by the difference in range between different locations on the surface of the object and the sensor. The relative range of an array of points on the surface of the object may be reconstructed by unwrapping phase information in the reflected images of the grating with respect to a designated origin or fiducial point. Range data of the array of points can be used to create a 3D surface image of the object.

As set out in the above referenced articles describing moiré topography, as well as other references in the literature, surface measurement of an object using moiré topography is well documented in the art. These references document current methods of making measurements on inanimate and animate objects, including living or preserved ears of experimental animals, human cadaver ears or in some cases the living human ear. However, known surface measurement techniques of living membrane using projection moiré topography utilize relatively large bench top instruments under laboratory conditions to measure the shape of the living membrane. These laboratory instruments have not been adapted for hand-held viewing of small, inaccessible, unaugmented living tissue, such as the tympanic membrane, in a clinical environment. Also, data resulting from the contour measurements is generally processed over periods of hours or days. In no known projection moiré topography technique have optical measurements of the contour, range and motion of the tympanic membrane, or other living tissue or structure, been made in near real time with a hand-held instrument which permits simultaneous visualization of the membrane.

Furthermore, laboratory moiré analysis of living membranes generally requires that the membrane be contrast-enhanced with, for example, white paint, to improve the diffuse reflectivity of the membrane. Additionally, moiré topography instruments require that movement of the living membrane be restrained during measurement. All of these requirements are not desirable or practical for measuring the surface topography of a living membrane of a patient during a clinical examination.

SUMMARY OF THE INVENTION

The present invention is of an apparatus for and method of determining topography of a living structure comprising: generating and directing an optical beam along a projection pathway; projecting the optical beam through a projection lens onto the structure; collecting reflected light from the structure in a detector along a detecting optical pathway; and generating topography of the structure from the reflected light collected by the detector. The preferred embodiment further comprises the step of collecting reflected light (simultaneous with generating topography of the structure) from the structure by viewing optics along a viewing optical pathway to view the structure. Collecting reflected light from the structure by viewing optics preferably comprises generating an image of the structure by a viewing lens and viewing the image of the structure generated by the viewing lens through an eye piece of an otoscope. The structure may be a viscera of a body, conjunctiva and cornea of an eye, pinna, external auditory meatus, mucosae of a body, parietal and visceral pleurae, or tympanic membrane of an ear. The preferred embodiment also provides for generating an image of the structure and recording the topography of the structure. Collecting reflected light from the structure in a detector preferably comprises collecting reflected light from the structure in a collecting lens and focusing the collected light onto the detector. Generating and directing an optical beam, projecting the optical beam, collecting reflected light from the structure are preferably performed within an otoscope. The topography of the structure is generated preferably by the use of an associated computer system for image and data processing used in conjunction with the otoscope. The invention preferably provides for diagnosing the condition of the structure after generating topography of the structure, such as by tracking changes in the structure over time, comparing a contour of an image of the structure with a contour selected from the group consisting of normative images of a structure and images of the structure from another point in time, and detecting swellings, depressions, and perforations in the structure. The preferred embodiment comprises image processing to convert data from the detector into an image of a contour map of the surface shape of the structure.

The present invention is also of an apparatus for and method of observing a tympanic membrane comprising: generating and directing an optical beam along a projection path; projecting the optical beam through a projection lens onto the membrane; collecting reflected light from the membrane in a first collecting lens along a detecting optical pathway; directing the reflected light from the first collecting lens to a detector; generating data about the membrane from the reflected light received by the detector; sending the data from the detector to an image processing system; and converting the data into a 3D image of the surface of the membrane. The preferred embodiment provides for collecting the reflected light from the membrane in a second collecting lens along a viewing optical pathway; directing the reflected light from the second collecting lens to viewing optics to generate a two-dimensional (2D) image of the membrane; viewing the 2D image of the membrane generated by the viewing optics through a viewing lens; and generating a recorded image of the membrane. Preferably, generating and directing an optical beam, projecting the optical beam, collecting reflected light from the membrane, directing the reflected light from the collecting lens, and generating an image of the membrane, are all performed within a hand-held otoscope, and an image of the membrane is generated by the viewing optics through an eye piece of an otoscope. The tympanic membrane may be in a living human or animal, and the invention preferably includes diagnosing a condition of the ear by tracking changes in the tympanic membrane over time, comparing a contour of an image of the membrane with a contour from the group consisting of normative images of a tympanic membrane and images of the tympanic membrane from another point in time, or detecting by processing swellings, depressions, and perforations in the tympanic membrane.

The invention is further of a device for and method of characterizing a condition of an object, comprising: generating an optical beam from an illumination source; spatially modulating the optical beam; projecting the modulated optical beam onto the object by a first gradient index lens responsive to the modulated optical beam; and providing data for characterization of the object from reflected light via a detector responsive to the reflected light from the object along a detecting optical pathway. In the preferred embodiment, the spatial modulation is done by employing a grating, and projecting comprises employing a cylindrical gradient index lens having first and second substantially flat end surfaces, the gradient index lens having a decreasing index of refraction from a central axis to an outer surface of the lens. A second gradient index lens is preferably employed responsive to the reflected light from the object so as to direct the reflected light onto the detector. Detection involves employing a camera comprising an array of charge coupled devices defining individual pixels positioned to form an image of the object, wherein the camera converts intensity distributions of the reflected light beam into electrical signals to form the image of the object. The invention preferably employs a processor responsive to electrical signals from the detector indicative of the condition of the object, the processor comprising moiré topography processing systems that convert the electrical signals from the detector into a three-dimensional (3D) image of the surface of the object. Phase contour lines of the object are generated by unwrapping phase data to provide a continuous contour map to eliminate ambiguities between adjacent cycles of the phase of the grating. A data storage and transmission system is employed with components from the group consisting of floppy disks, hard drive storage methods, hard copy printers, video displays, and transmitters. A grating drive operable to position the grating at multiple locations during determination of topography of the object is preferably employed, wherein the multiple locations of the grating are within a plane of grating lines of the grating and the distance between the locations is a fraction of a fringe distance of the grating lines. Viewing optics are best utilized, wherein the reflected light impinges the viewing optics to be viewed by an operator, the viewing optics are positioned along a viewing optical pathway separate from the detecting optical pathway. The invention may be employed to measure a surface shape of a tympanic membrane of an ear with an otoscope comprising a body, an optical head, a speculum, and an eye piece. The illumination source may be within the body, measuring may comprise positioning the detector within the body, positioning the first gradient index lens within the speculum, and positioning a pneumatic pathway within the speculum. Multiple gradient index lenses provide separate optical pathways, generating comprises employing an illumination source comprising a non-coherent, white light source. The object may be any natural or manufactured object, any living biological tissues or organs in situ, viscera of a body, epidermis of a body, teeth of a mouth, an eye, a nose, mucosae of a body, or parietal and visceral pleurae.

The invention is additionally of a device for and method of determining contour of a living structure, comprising: generating and transmitting an optical beam along a projection path to impinge the structure, via an illumination source; creating a spatially modulated optical beam that produces light and dark fringe patterns on the structure, via a grating positioned along the projection path and modulating the optical beam; providing electrical signals of intensity variations of a reflected beam, via a detector positioned along a detection path, the detector responsive to the reflected light beam from the structure; and employing a processor responsive to electrical signals from the detector indicative of an image of the structure, the processor including moiré topography processing means that convert the electrical signals from the detector into a contour map of a surface shape of the structure. In the preferred embodiment, the invention further comprises positioning viewing optics along a viewing path, the viewing optics being responsive to the reflected light beam from the structure so as to provide viewing of the structure by an operator, positioning a first gradient index lens along the projection path, the first gradient index lens being responsive to the modulated optical beam from the grating so as to project an image of the grating onto the living structure, a second gradient index lens positioned along the detection path so as to project the reflected light beam onto the detector, and a third gradient index lens positioned along the viewing path so as to project the reflected light beam onto the viewing optics. The first gradient index lens is preferably a cylindrical gradient index lens having first and second substantially flat end surfaces and a decreasing index of refraction from a central axis to an outer surface of the cylindrical gradient index lens. A camera is preferably provided comprising an array of charge coupled devices defining individual pixels to form the image of the structure, the camera converting intensity distributions of the reflected light beam into electrical signals to form the image of the structure. A grating drive is preferably employed, operable to position the grating at multiple locations during a contour measurement of the structure, wherein the multiple locations of the grating are within the plane of grating lines of the grating and the distance between the locations is a fraction of the line spacing distance of the grating line projected on the structure. An otoscope is preferably employed to measure a surface shape of a tympanic membrane of an ear, the otoscope comprising a body, an optical head, a speculum, and an eye piece, generating and transmitting preferably comprises employing an illumination source positioned within the body in which the grating and detector are positioned, with the viewing optics being within the optical head. A data storage or transmission system with elements from the group consisting of floppy disks, hard drive storage methods, hard copy printers, video displays, and transmitters is preferably employed. The structure is preferably a tissue of a body, a viscera of a body, conjunctiva and cornea of an eye, pinna, external auditory meatus, tympanic membrane of an ear, mucosae of a body, or parietal and visceral pleurae.

The invention is also of an otoscope and method for measuring a shape of a tympanic membrane, comprising: selecting an otoscope body; configuring a speculum to be inserted within an ear canal, the speculum being secured to the otoscope body;

securing an eye piece to the otoscope body opposite from the speculum; positioning an illumination source within the otoscope body, the illumination source generating an optical beam; positioning a grating within the otoscope body, the grating blocking the optical beam so as to generate a modulated optical beam; providing a grating drive, the grating drive operable to position the grating at multiple locations during a measurement of the tympanic membrane, wherein the multiple locations of the grating are along a plane of grating lines of the grating and a distance between the locations is a fraction of a line spacing distance of the grating lines; positioning a first gradient index lens within the speculum, the first gradient index lens being responsive to the modulated optical beam so as to project phase-stepped images of the grating onto the tympanic membrane; positioning viewing optics along a viewing pathway, the viewing optics being responsive to reflected light from the tympanic membrane along the viewing pathway to provide an image of the membrane to the eye piece; positioning a camera within the otoscope body, the camera being responsive to the reflected light from the tympanic membrane along a detecting optical pathway, the camera converting intensity variations of the reflected light into indicative electrical signals so as to provide an image of the membrane; and supplying a processor responsive to the electrical signals from the camera, the processor, including moiré topography processing means, that converts the electrical signals from the camera into a contour map of a surface shape of the membrane. In the preferred embodiment, the first gradient index lens (length of approximately 5 cm and a diameter of approximately 1 mm) is a cylindrical gradient index lens having first and second substantially flat end surfaces and an index of refraction that descends from a central axis to an outer surface of the cylindrical gradient index lens, and second and third gradient index lenses are employed, the second gradient index lens being positioned along the detecting pathway so as to project the reflected light onto the camera, and the third gradient index lens being positioned along the viewing pathway so as to project the reflected light onto the eye piece. The camera comprises an array of charge coupled devices defining individual pixels to form the image of the membrane. The processor is a moiré topography processing system which includes a phase algebra algorithm that generates contour lines of the membrane based on a phase of the grating, and a phase unwrapping algorithm that provides a continuous contour map to eliminate ambiguities between adjacent cycles of the phase of the grating, and includes elements from the group of floppy disks, hard drive storage, hard copy printouts, video displays and transmitters.

The invention is further of a device for and method of determining topography of an object, the method comprising the steps of: generating an optical beam; projecting the optical beam through a grating so as to create a projected optical beam having a grating pattern; projecting the optical beam having the grating pattern onto a first gradient index lens so as to project an image of the grating onto the object; and collecting reflected light from the object in a detector along a detecting optical pathway to provide topography of the object. In the preferred embodiment, a moiré topography processing system converts data from the detector into an image of a contour map of the surface shape of the object, the grating is moved to multiple locations (rapidly) during determination of topography of the object, wherein the multiple locations of the grating are along the plane of the grating lines and the distance between the locations are a fraction of the period of the grating lines, and viewing optics are provided so as to view the object simultaneously with the step of generating an image of the object.

The invention is additionally of a device for and method of measuring a shape of an object, the method comprising the steps of: generating an optical beam with a hand-held apparatus; projecting the optical beam onto the object; collecting reflected light from the object in a detector along a detecting optical pathway within the hand-held apparatus; analyzing by optical metrology in near real time the collected light; and providing a contour map of a surface shape of the object based on the analysis. In the preferred embodiment, analyzing is performed by an optical metrology technique from the group consisting of wave front sensing, infrared or visible light stereographic topography, laser Doppler velocimetry, moiré topography, homodyne and heterodyne interferometry, and target-based interferometry. The object may be a living tissue. Generating an optical beam is preferably done using a hand-held device.

The invention is also of a device for and method for measuring the shape of an object, the method comprising the steps of: providing a hand-held body; supplying an illumination source, the illumination source generating an optical beam; modulating the optical beam to generate a modulated optical beam; positioning a lens responsive to the modulated optical beam to project an image onto the object; and utilizing a detector responsive to reflected light from the object along a detecting optical pathway, the detector providing an image of the object in near real-time. In the preferred embodiment, supplying an illumination source, modulating the optical beam, positioning the lens, and utilizing the detector occur within the hand-held body.

The invention is further of a method of examining the ear of a patient, comprising: pulling the pinna of an ear of the patient gently in a caudal and superior direction to straighten an external auditory meatus; providing a speculum on a head of a hand-held quantitative otoscope; illuminating the external auditory meatus with a light source of the hand-held quantitative otoscope through a projection pathway; inserting the speculum into the external auditory meatus of a patient to view a tympanic membrane; noting topography of the tympanic membrane; and capturing an image of the tympanic membrane through a collection pathway of the hand-held quantitative otoscope via an image processing computer system. In the preferred embodiment, the image of the tympanic membrane is viewed on a video monitor, and the relevant data is saved on storage media.

The invention is additionally of an otoscope comprising a gradient index lens. In the preferred embodiment, the gradient index lens is responsive to a modulated optical beam and is positioned to project an image of a grating onto an object. The gradient index lens comprises a cylindrical gradient index lens having first and second substantially flat end surfaces, the gradient index lens having a decreasing index of refraction from a central axis to an outer surface of the lens.

It is a primary object of the present invention to provide a hand-held measurement device for providing real time observations of an object, animate or inanimate.

It is another object of the present invention to provide a hand-held otoscope for providing real time static and dynamic observations of a living structure by a phase-stepped projection moiré topography technique that also allows simultaneous record storage of the observations and visualization of the structure by a user.

Additional objectives, advantages and features of the present invention will become apparent from the following description and appended claims made in conjunction with the accompanying drawings.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE PREFERRED EMBODIMENTS

The invention relates to a hand-held, near real-time device for making static and dynamic measurements of a surface by optical metrology techniques, such as wave front sensing, wave front sensing with deformable mirrors, infrared or visible light stereographic topography, laser Doppler velocimetry, homodyne or heterodyne interferometry, target-referenced interferometry, and preferably moiré topography. The following description of the preferred embodiments directed to a projection moiré topography otoscope and method to measure the contours of a living structure is merely exemplary in nature and is in no way intended to limit the invention or its applications or uses.

Figure 1:
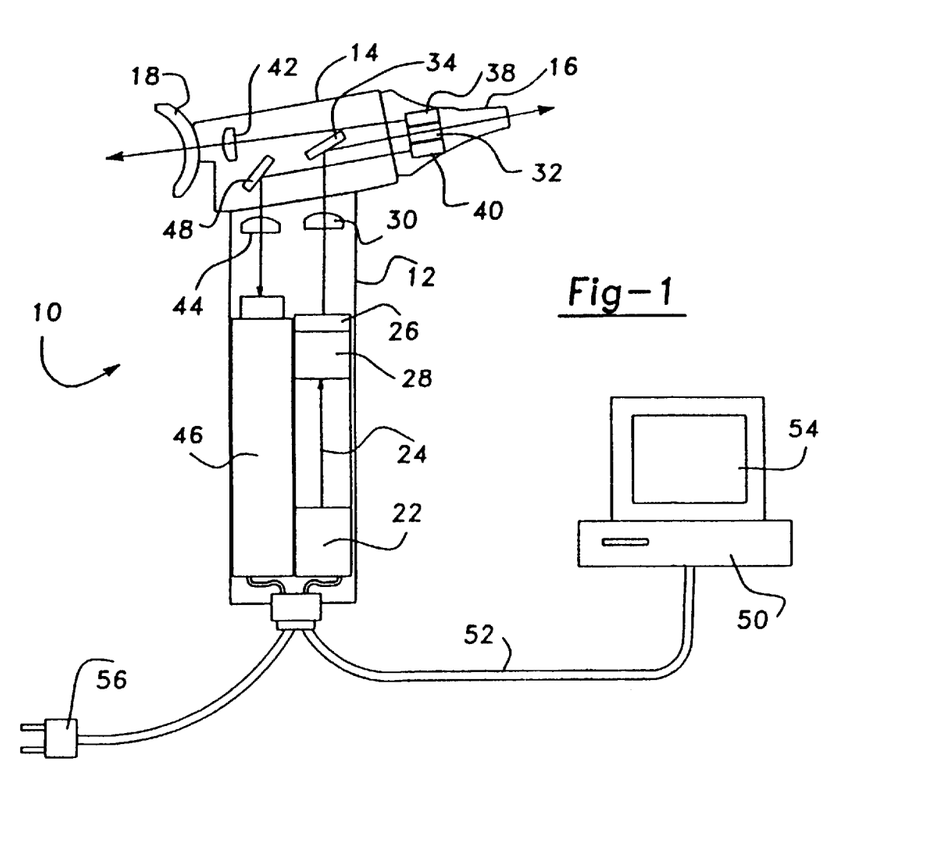
FIG. 1 is a diagrammatic plan view of an otoscope according to embodiment of the present invention.

First turning to FIG. 1, a diagrammatic view of a quantitative otoscope 10 according to an embodiment of the present invention is shown. The otoscope 10 includes a hollow cylindrical body 12 attached to an optical head 14. A speculum 16, preferably hollow, cone-shaped and composed of plastic, is connected to one end of the optical head 14 and an eye piece 18 (e.g., made of rubber or resilient material) is connected to an opposite end of the optical head 14. The otoscope 10 is of the size and shape of conventional otoscopes known in the art. The speculum 16 is inserted into a patient's ear canal (not shown) so a physician can view the patient's ear canal and tympanic membrane through the eye piece 18. The speculum 16 is preferably removably attached by a mount to the otoscope 10. The optical head 14 includes a pneumatic pathway (such as a metallic tube) for providing calibrated pneumatic stimuli to the ear canal from a pneumatic pressure device, such as a bulb squeezed manually to develop pressure. The pneumatic pathway conveys the pressure wave through the aperture of the speculum to the ear canal. A range of specula 16 are preferable, having varying diameters, preferably from 2.0 mm to 7.0 mm for viewing different sized and shaped human ears. Additionally, as will become apparent from the discussion below, the otoscope 10 includes a number of features that allow the physician to provide a quantitative analysis of the health of the patient's middle ear area.

The otoscope 10 includes an illumination source 22 preferably positioned within the otoscope body 12. The illumination source 22 can be any applicable illumination source known in the art suitable for the purposes described herein, and preferably is a non-coherent, inexpensive white light source. The illumination source 22 emits an optical beam 24 that propagates through a lined grating 26. In one embodiment, the grating 26 is a Ronchi grating, known to those skilled in the art, having equally spaced transparent and opaque stripes. A precision grating drive device 28 is connected to the grating 26 to provide stepped positional movements of the grating 26 during measurements. As will be discussed in greater detail below, for each measurement of the patient's tympanic membrane, the grating 26 is precisely and rapidly positioned to three different locations, where the difference between the locations is based on a fraction of the period of the lines in the grating 26.

The optical beam 24 then impinges an objective lens 30 to be focused onto a gradient of refractive index (GRIN) lens 32 after being re-directed by folding optics 34 in the optical head 14, as shown. The GRIN lens 32 projects and focuses the grating onto the patient's tympanic membrane through the speculum 16. The grating projected on the tympanic membrane provides a pattern of light and dark fringes on the membrane that is dependent on the spacing of the grating lines of the grating 26 and the shape of the membrane. The speculum 16 preferably includes multiple GRIN lenses to mediate matching multiple optical pathways. In the preferred embodiment, there are three GRIN lenses, one lens 32 for projecting the optical beam 24 on the membrane, another lens 38 for providing direct viewing by the user and another lens 40 for providing camera viewing and/or recording. As can be seen, a fewer or greater number of lenses can be provided to eliminate or enhance viewing devices, calculations or presentations.

Figure 2A:
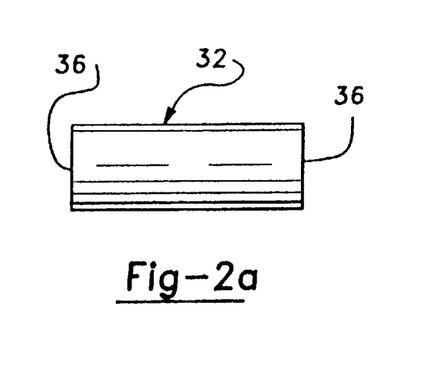
FIG. 2(a) is a side view and FIG. 2(b) is an end view of a gradient index lens associated with the otoscope of FIG. 1.
Figure 2B:
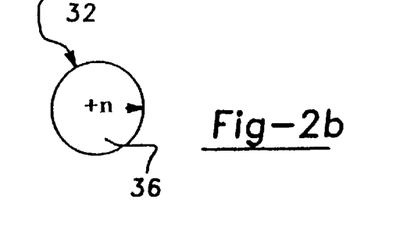

A GRIN lens is a known lens that provides light focusing by an optical material having a varying index of refraction. FIG. 2(a) shows a side view and FIG. 2(b) shows an end view of a typical GRIN lens 32. The GRIN lens 32 is a cylinder of an optical plastic or glass such that the index of refraction varies with the distance from the cylinder axis and where end faces 36 of the lens 32 are flat. The lens 32 is a converging lens where the outermost part of the cylinder has the lowest index of refraction and the innermost part has the highest index of refraction, such that the index of refraction n decreases from the innermost part to the outermost part. Such a lens provides a number of advantages for the purposes of the present invention, including long lens lengths where the lens itself can be several centimeters long, so as to provide access into the ear canal. In the embodiment shown, the GRIN lens 32 has a length of about 5 cm and a total diameter of about 1 mm.

Light reflected from the tympanic membrane is collected in the speculum 16 and is focused by a GRIN lens 38 and another GRIN lens 40. Reflected light collected by the GRIN lens 38 is focused onto a viewing lens 42 to be observed by the user through the eye piece 18. Reflected light collected by the GRIN lens 40 is focused by a camera lens 44 onto a TV camera 46 preferably within the optical body 12 after being re-directed by folding optics 48 in the optical head 14. The camera 46 can be a charged coupled device (CCD) camera where an array of CCDs of the camera 46 measure the light intensity at a particular location to provide a series of pixels (picture elements) of the total image of the membrane. Cameras of this type provide a high degree of resolution and are well known to those skilled in the art. In this manner, the tympanic membrane of the patient's ear can be simultaneously viewed by the physician or operator and recorded by the camera 46 in real time.

Light intensity information processed by the camera 46 is applied to a personal computer (PC) 50 through an electrical cable 52. Associated with the PC 50 is a video screen 54 that gives a near real-time image of the contour, shape, range, and motion by moiré topography of the tympanic membrane during the examination. The PC 50 includes specialized signal processing software and hardware, discussed below, to carry out the extensive data manipulation required for optical metrology in the shortest possible time. Optical data are analyzed and displayed on the video screen 54 as a high resolution surface image of the tympanic membrane along with information about the color spectrum of the light reflected from an array of points on the membrane. This information may be saved as a hard copy from a printer (not shown) and as a digital file on a storage medium within the PC 50. The digital file including data and images becomes part of the patient's medical record.

In this embodiment, the otoscope 10 is powered by a plug-in power cable 56. Although conventional otoscopes are generally battery operated, the bulk of space within the body 12 is taken up by the illumination source 22, the drive device 28 and the camera 46. Therefore, the otoscope 10 is powered by an exterior power source in this example. If desirable, the length of the body 12 can be extended to incorporate a suitable battery pack. Additionally, the otoscope 10 can be powered by the PC 50 through the cable 52.

The invention thus far has been discussed with reference to an otoscope for observing and measuring the contours of the tympanic membrane of a patient. However, it is stressed that the invention has application to other living structures, such as nose and throat membranes, in conjunction with other types of medical instruments (e.g., endoscopes) used for these purposes. The invention has particular application for viewing living structures where the entrance aperture to the structure is small, e.g., below 5 mm. Likewise, the invention is useful for other inside and outside surfaces, both animate and inanimate, where a hand-held, real-time device provides convenient use. Although not shown, a switch is provided to activate the system when the operator is ready to take measurements of the membrane or tissue.

Figure 3:
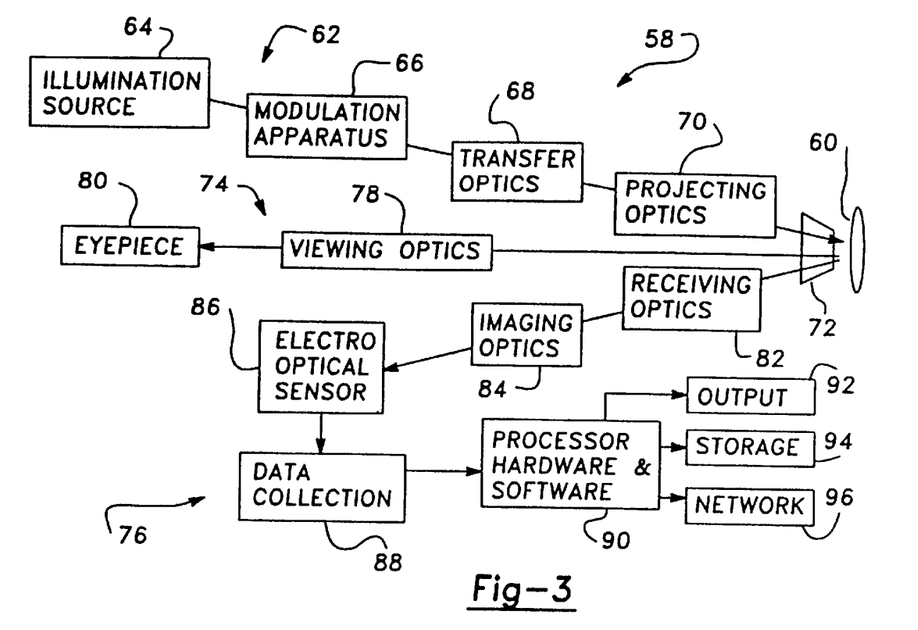
FIG. 3 is a block diagram depicting the operation of three optical paths within the otoscope of FIG. 1.

FIG. 3 shows a block diagram 58 depicting the operation of the invention along each of three different optical paths through the device when measuring the surface contours of an object 60. A projection path 62 includes an illumination source 64, e.g., the illumination source 22 of the otoscope 10 shown in FIG. 1. The illumination source 64 may include different features for different applications including enhanced brightness, wavelength filters, stroboscopy, etc., as would be understood to those skilled in the art. A modulation apparatus 66 provides precision grating motion, for example amplitude modulation of the optical beam generated by the illumination source 64. Transfer optics 68 represents the different optical components, such as the objective lens 30 and the mirror 34 shown in FIG. 1. The transfer optics 68 may include suitable molded optical components and diffractive optical components for transmitting the optical beam through the device onto the object 60. Projecting optics 70 represents the GRIN lens 32 shown in FIG. 1 for focusing the optical beam 24 on the tympanic membrane through the speculum 72 or other focusing device.

Light reflected from the object 60 into the speculum 72 or focusing device is transmitted along a viewing path 74 and a sensing path 76. The viewing path 74 includes viewing optics 78 intended to represent the GRIN lens 40 and the lens 42 shown in FIG. 1, and an eye piece 80 intended to represent the eye piece 18 shown in FIG. 1. The sensing path 76 includes receiving optics 82 representing the GRIN lens 36 and the mirror 46 shown in FIG. 1, and imaging optics 84 representing the camera lens 44 shown in FIG. 1. The reflected beam on the sensing path 76 is then sensed by an electro-optical sensor 86, such as the CCD camera 46 shown in FIG. 1. The electro-optical sensor 86 provides electrical signals for an array of pixels indicative of the intensity of the reflected beam, and provides these electrical signals to a data collection unit 88, such as PC 50. Processor hardware and software 90 represents the internal processing devices within the PC 50 that provide appropriate signals to a series of output sources. These output sources include an output source 92, such as a video display or a hard copy, a storage output 94, such as a hard disk or a floppy disk, and a network output 96 such as a transmission to a remote source.

It is noted that the transfer optics 68, the viewing optics 78, the receiving optics 82 and the imaging optics 84 are intended to represent the optics necessary for transmitting the optical beam to the object 60, and the reflected beam from the object 60 to the eye piece 80 and the optical sensor 86. These optics may vary from otoscope to otoscope, or instrument to instrument, depending on the particular application. Therefore, these different optics may be different than those illustrated in FIG. 1 for alternative embodiments within the scope of the invention.

Contour measurement of an object by projection moiré topography is well documented in the literature. Various techniques and concepts within the scope of moiré topography provide surface shape measurements for a wide range of different objects. In projection moiré topography, an appropriate lined grating is projected onto an object to be measured to create light and dark moiré fringes on the object having a phase determined by the spacing of the grating lines and the shape of the object. A mathematical relationship of the phase of the fringe pattern can be generated with respect to the surface of the object. If the object were perfectly flat, the bright and dark fringe lines on the object would appear as straight lines. For an object that is not flat, the lines are bent, and the phase of the fringes are altered with respect to the mathematical relationship of the phase pattern of a flat object. This change can be measured as changes in the sensed intensity of the reflected optical beam. The phase of the fringe pattern created by the shape of the surface of the object can then be calculated and converted to range differences, thus giving a mathematical representation of the surface shape of the object. A more detailed discussion of this process can be found in the Tasaki, H. and the Dirckx, J. J. J., et al. articles referenced above.

The present invention provides a phase analysis of patterns of light reflected off the object. The phase differences with respect to a designated origin are used to provide information about the object surface. Although the shape of an object can be measured by moiré topography processes when the grating is at a single location, it has been shown in the literature that a much more accurate shape representation can be achieved by taking measurements of the object with the grating at three locations within the plane of the grating. It has been shown that the displacement of the grating should be a fraction of the period of the grating. By taking moiré topography measurements at these three locations, three different representations of the object can be generated so that unknown quantities, such as reflectivity effects from the object and background noise, can be reduced.

Several digital signal processing procedures are used in a unique combination to compensate for or circumvent the fact that most of a tympanic membrane, with the exception of a cone-shaped zone near the umbo, reflects only a small percentage of incident light and has low intrinsic contrast. These procedures include brightness (amplitude) ratioing to compensate for non-uniform reflectance, non-linear digitization to improve the signal-to-noise ratio in phase data at the expense of amplitude data for large signals, and two-dimensional spatial filtering to create a band pass filter about the grating frequency to reduce noise.

Changes in the range of the tympanic membrane evoked by calibrated pneumatic stimuli in the ear canal can be measured to provide a two-dimensional map of tympanic membrane compliance. The relative range of an array of points on the surface of the tympanic membrane may be reconstructed by unwrapping phase information in the reflected images of the grating with respect to a designated origin or fiducial point. The range data for the array of points are used to create a graphic display of the surface of the tympanic membrane. This embodiment gives a topography measurement resolution of less than 100 $\mu$m.

Figure 4:
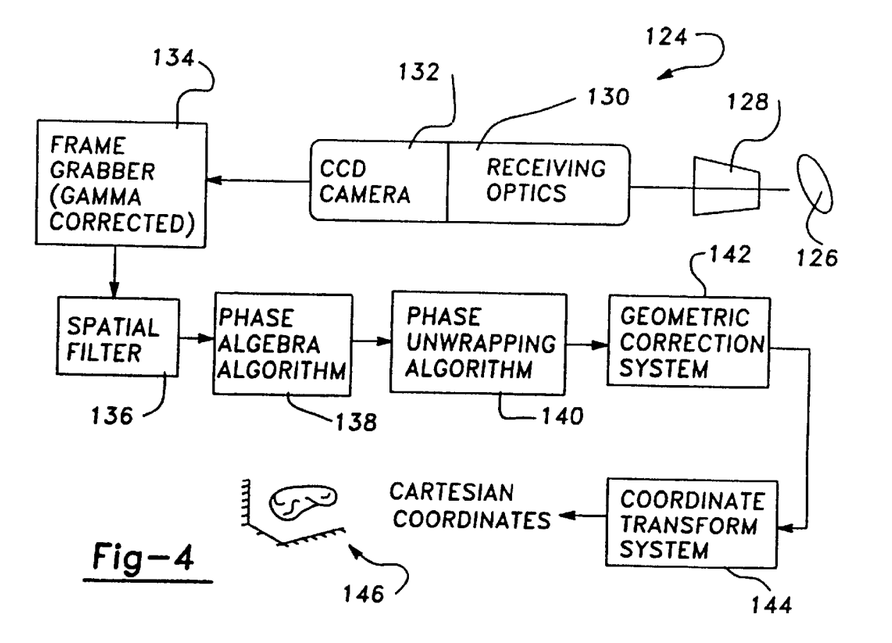
FIG. 4 is a block diagram depicting the operation of a projection moiré topography technique for measuring the surface shape of a living structure.

FIG. 4 shows a block diagram of the preferred signal processing for projection moiré topography of the invention that provides the above features. Reflected light from an object (e.g., a tympanic membrane) 126 is collected in a speculum or other focusing device 128 to be received by receiving optics 130. The receiving optics 130 focus the light onto a detector, such as a CCD camera 132. The CCD camera 132 generates electrical signals for each pixel of an image frame, and applies these signals to a frame grabber 134. The frame grabber 134 converts the electrical signals from the camera 132 into digital signals suitable for subsequent processing of the system. Further, the frame grabber 134 provides linearity correction (gamma correction) of the light intensity signals from the camera 132 in the event that the camera 132 is not a linear device. Processing with a spatial filter 136 is then applied to the gamma corrected digital frame data to provide enhanced modulation of the grating image for noise filtering purposes. The preferred implementation of this spatial filtering is a finite impulse response (FIR) filter, as is well understood in the art. The digital signals representing the sequence of grating shifted frames of data from the spatial filter 136 are then applied to a phase algebra algorithm 138 to derive the modulation phase for each pixel in the image. The phase algebra system 138 generates the representative contour lines of the tympanic membrane 126 based on the phase of the grating for all of the pixels in the image, and provides a representative map of the object based on these phase differences. The preferred processing procedures for this phase algebra algorithm are those described in Dirckx, J., et al. "Phase Shift Method Based on Object Translation for Full Field Automatic 3-D Surface Reconstruction From Moiré Topograms," APPLIED OPTICS, Vol. 27, No. 6, Mar. 15, 1988, pp. 1164–1169.

The phase map signals are then applied to a phase unwrapping algorithm 140 to correct for phase discontinuities. The phase unwrapping system 140 reconstructs the relative range of an array of points on the surface of the object 126 and provides a continuous map of the object 126 so as to correct for ambiguities (particularly 2$\pi$ ambiguities) between adjacent cycles of the phase relationship of the grating lines projected on the object 126. The preferred processing procedures for this phase unwrapping algorithm are those described in Takajo, Hiroaki and Takahasji, Tohru, "Noniterative Method for Obtaining the Exact Solution for the Normal Equation in Least-Squares Phase Estimation From the Phase Difference," Journal of the Optical Society of America, Vol. 5, No. 11, November 1988, 1818. Spatial resolution of the array of points of the contour map is at least 64×64 in this example and is only limited by the optical resolution and CCD pixel spacing.

The unwrapped phase signals are then applied to a geometric correction system 142 that applies non-linear phase correction to the signal. The geometric correction system 142 provides calibration to the signal as the result of beam expansion that may alter the phase as a function of range in the beam. The preferred processing procedure for this system is an adaption of that presented in Dirckx, J., and Decraemer, W., "Automatic Calibration Method for Phase Shift Shadow Moiré Interferometry," APPLIED OPTICS, Vol. 29, No. 10, 1 Apr. 1990, 1474–1476. The preferred approach must, due to the unique geometry of the present invention, account for more significant non-linearities than those considered in the reference. An output of the geometric corrector 142 is in range and angle coordinates which are then converted to Cartesian coordinates by a coordinate transform system 144. The processing procedures for this coordinate transform system are well known to those skilled in the art. The Cartesian coordinate system can then be displayed as a 3D surface image display 146 showing the object (e.g., tympanic membrane) 126 from an arbitrary viewpoint. The 3D surface image may also incorporate the 2D color image recorded at the camera to present a 3D color rendition of the measured object. Each of the operations discussed above with reference to the frame grabber 134, the spatial filter 136, the phase algebra algorithm 138, the phase unwrapping algorithm 140, the geometric correction system 142 and the coordinate transform system 144 are all operations that can be performed in the hardware and software of a PC. The general operations are typical to known moiré topography systems and would be well understood to those skilled in the art.

The discussion above has been directed to surface mapping of a tympanic membrane. However, the moiré topography method of the invention, in conjunction with the associated optics, can be used to view and record any membranes or tissues, or inanimate objects, in association with a suitable device to provide real-time analysis of the object. The moiré topography method of the invention is particularly adaptable to real-time clinical analysis of small, fairly inaccessible structures of the human or animal body.

As discussed above, the grating drive device 28 must precisely position the grating 26 in three locations for each contour measurement. In order to be practical for a small instrument, such as the otoscope 10, it must be small enough to fit easily within the instrument body and be relatively inexpensive. The grating drive device 28 must rapidly and accurately position the grating so that movement by the operator of the otoscope 10, and movement of the tympanic membrane during measurement, do not affect the tympanic membrane shape calculations. In one example according to the invention, the grating drive device 28 displaces the grating 26 in three phase steps of 120° each at a rate of 16 msec or less per step. Therefore, the grating drive device 28 must be assembled from low-cost components that are small and reliable. Different systems can be devised to meet these requirements. In one embodiment, the grating drive device 28 may include liquid crystal displays that are electrically actuated to alter the grating line positions in a grating display. Other applicable grating drive systems make use of piezoelectric actuators.

Figure 5A:
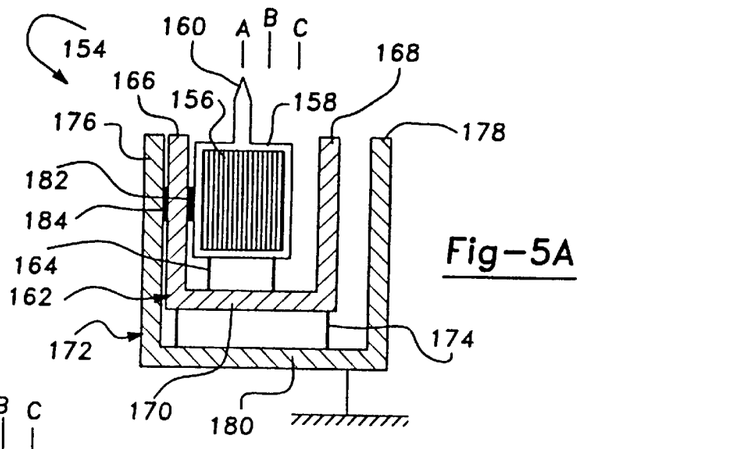
FIGS. 5(a)-5(c) depict diagrammatic views of a model grating drive device according to an embodiment of the present invention.
Figure 5B:
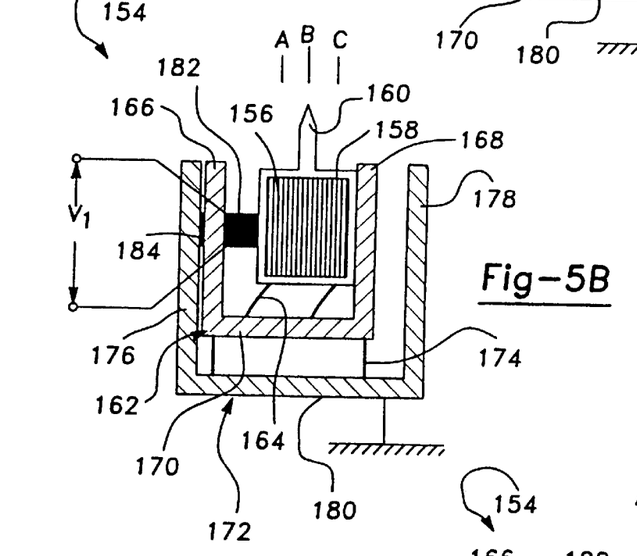
Figure 5C:
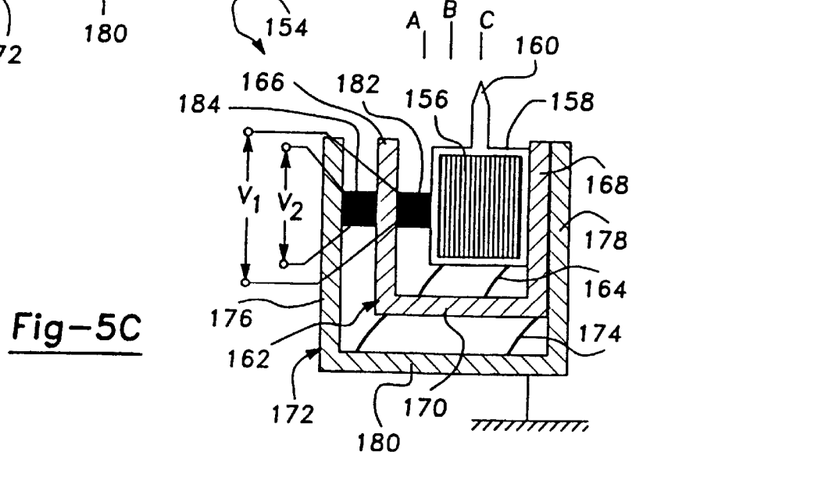

FIGS. 5(a)–5(c) show a diagrammatic view of a grating drive 154 that can be used as the drive device 28 according to an embodiment of the present invention. The grating drive 154 includes a grating 156 positioned on a grating platform 158. A pointer 160 extends from the platform 158 to indicate at what location the grating 156 is positioned. The grating platform 158 is secured to an inner conductive cage 162 by a pair of resilient metal leaf springs 164 as shown. The inner cage 162 includes a left-side wall 166 and a right-side wall 168 connected to a base 170. The leaf springs 164 are connected to the platform 158 and the base 170 as shown. The inner cage 162 is secured to a grounded outer conductive cage 172 by a pair of resilient metal leaf springs 174 as shown. The outer cage 172 includes a left-side wall 176 and a right-side wall 178 connected to a base 180. The leaf springs 174 are connected to the base 170 of the inner cage 162 and the base 180 of the outer cage 172. The leaf springs 164 allow the grating platform 158 to be resiliently positioned at different locations within the inner cage 162. Likewise, the leaf springs 174 allow the inner cage 162 to be resiliently positioned at different locations within the outer cage 172.

Figure 6A:
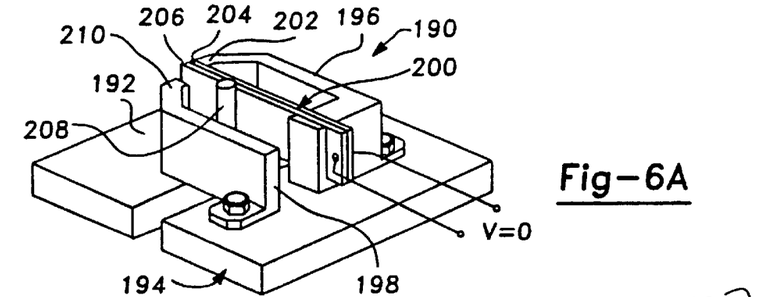
FIGS. 6(a)-6(b) show perspective views of a piezoelectric bimorph actuator for use in a miniature grating drive device of the invention.

A first piezoelectric actuator 182 is positioned between the left-side wall 166 of the inner cage 162 and the grating platform 158, and a second piezoelectric actuator 184 is positioned between the left-side wall 176 of the outer cage 172 and the left-side wall 166 of the inner cage 162. When both of the piezoelectric actuators 162 and 176 are in their relaxed state, i.e., no voltage potential is applied to the actuator 182 and 184, the grating platform 158 is positioned adjacent the left-side wall 166 within the inner cage 162, and the inner cage 162 is positioned adjacent the left-side wall 176 within the outer cage 166 as shown in FIG. 6(a). In this position, the leaf springs 164 and 174 are also in their relaxed state. At this location the pointer 160 indicates that the grating 156 is at position "A".

Figure 6B:
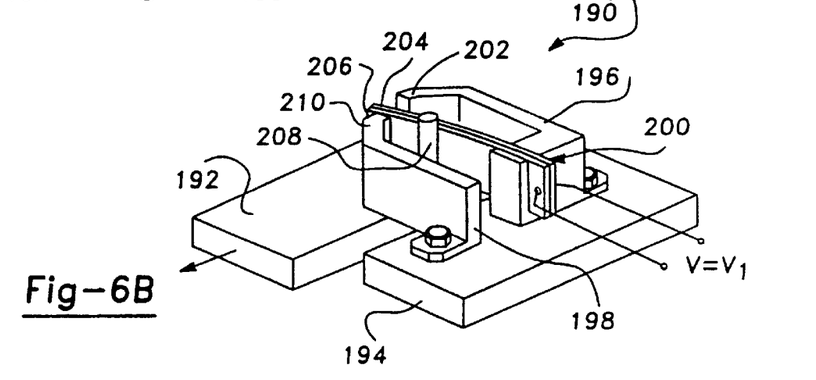

By grounding the outer cage 172 and applying a suitable voltage potential $V_1$ to the first actuator 182, the first actuator 182 expands against the resiliency of the leaf springs 164 such that the leaf springs 164 bend causing the grating platform 158 to move across the inside of the inner cage 162 and contact the right-side wall 168 of the inner cage 162, as shown in FIG. 6(b). When the grating platform 158 is in this position, the pointer 160 indicates that the grating 156 is at the "B" position. If the voltage $V_1$ is maintained on the piezoelectric actuator 182, and a suitable voltage potential $V_2$ is applied to the piezoelectric actuator 184, the actuator 184 will expand against the resiliency of the leaf springs 174 such that the leaf springs 174 bend causing the inner cage 162 to move towards the right within the outer cage 172 until the right-side wall 168 of the inner cage 162 contacts the right-side wall 178 of the outer cage 172, as shown in FIG. 6(c). When the inner cage 162 is in this position, the pointer 160 indicates that the grating 156 is positioned at location "C". In this manner, the grating 156 can be accurately positioned at three locations very rapidly for contour measurements. Note that the leaf springs 164 and 174 are "stiff" so that the grating 156 and the inner cage 162 return to their relaxed position when the voltage potential $V_1$ and $V_2$ are removed. One of ordinary skill in the art would know how to program the PC 50 to provide the voltage potentials $V_1$ and $V_2$ at the appropriate time to the drive 154 to position the grating 156 at the desirable locations during contour measurements.

It should be noted that a fourth position is also realizable by the drive 154. Particularly, if the voltage $V_1$ is removed and the voltage $V_2$ is maintained, the inside piezoelectric actuator 182 will be relaxed such that the grating platform 158 will move back to the left-side wall 166 of the inner cage 162. If the distance between the positions "A" and "B", and the distance between the positions "B" and "C" are not equal, then this fourth position may be a unique position relative to the position "B".

The drive 154 represents a model of a grating drive suitable for the purposes of the present invention. One of the difficulties encountered in recording multiple images of a living structure is that the structure tends to move between the time the different images are recorded. Similarly, an operator of the otoscope 10 may not be able to hold the otoscope 10 steady while recording the images. For this reason, the three images necessary for each contour measurement must be obtained rapidly in comparison to the movement speed of the structure and the operator. This requirement implies that the grating drive must be capable of moving rapidly between the three required positions. Analysis has shown that the grating drive must be able to move the grating from one position to the next position in less than $\frac{1}{160}$ of a second. While piezoelectric actuators which operate on the principle depicted in FIGS. 5(a)–5(c) are capable of providing this requirement, the stroke and force required for the drive 154 may necessitate an actuator size which may not be compatible with a hand-held otoscope.

Turning to FIGS. 6(a)–6(b), perspective views of a piezoelectric bimorph actuator 190 are shown. The actuator 190 includes a payload 192 movable relative to a base 194. A first rigid limit stop 196 is secured to the base 194 at one location, and a second rigid limit stop 198 is secured to the base 194 at a second location relative to each other, as shown. A piezoelectric laminate 200 is secured to the limit stop 196, and contacts a stop edge 202 of the limit stop 196 when the laminate 200 is in a relaxed state, i.e., when the voltage potential applied to the laminate 200 is zero as shown in FIG. 7(a). The piezoelectric laminate 200 includes a first piezoelectric layer 204 and a second piezoelectric layer 206 of two different piezoelectric materials that expand differently under the influence of an electric field. The piezoelectric layer 204 and the piezoelectric layer 206 can be any piezoelectric material, known in the art, suitable for the purposes of the present invention. The two piezoelectric layers 204 and 206 are rigidly secured to each other. A bumper post 208 is rigidly secured to the payload 192 between the limit stop 198 and the piezoelectric laminate 200, as shown. Piezoelectric laminates of the type of laminate 200 are known in other types of piezoelectric actuators, for example, piezoelectric actuators that are commercially available piezoelectric bimorph actuators from Morgan-Matrok of Bedford, Ohio.

A zero voltage potential applied to the laminate 200 positions the payload 192 relative to the base 194 as shown in FIG. 6(a). If a suitable voltage potential $V_1$ is applied to the laminate 200, then the piezoelectric layer 204 will expand more than the piezoelectric layer 206 such that the piezoelectric laminate 200 bends toward the limit stop 198, applying pressure against the bumper post 208. Pressure against the bumper post 208 causes the payload 192 to move in the direction of the arrow as shown in FIG. 6(b). The laminate 200 will eventually contact a stop edge 210 of the limit stop 198 so that the travel of the payload 192 is set by the position of the limit stop 198 so as to accurately position the payload 192 when the voltage potential is applied to the piezoelectric laminate 122. The movement of the payload 192 can be controlled by shaving the stop edge 210. In this manner, the payload 192 can be accurately and quickly positioned at different locations for different applications.

Figure 7:
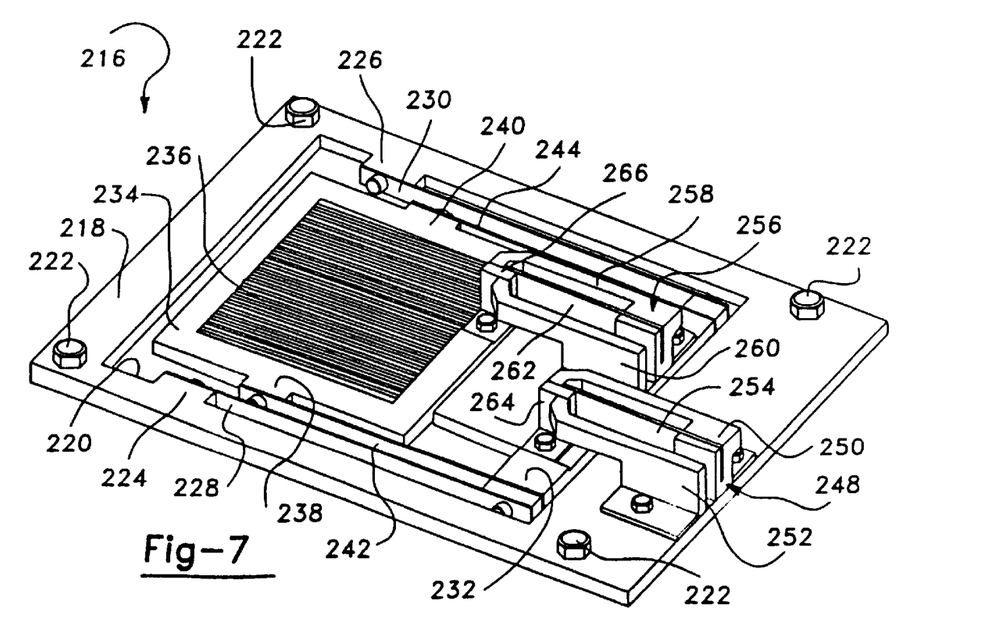
FIG. 7 shows a perspective view of a miniature grating drive device employing piezoelectric bimorph actuators according to the invention.

FIG. 7 shows a perspective view of a miniature grating drive (MGD) 216 according to an embodiment of the present invention. The MGD 216 includes an outer cage 218 defining an opening 220. A series of fasteners 222 enable the drive 216 to be secured in, for example, the otoscope body 12. A first tab member 224 and a second tab member 226 extend into the opening 220 as shown. A first outer leaf spring 228 and a second outer leaf spring 230 are secured to the tab members 224 and 226, respectively, and to an inner cage 232 positioned within the opening 220 as shown. A grating platform 234 holding a grating 236 is positioned within the opening 220 adjacent to the inner cage 232. The grating platform 234 includes a first tab member 238 positioned adjacent to the tab member 224 and a second tab member 240 positioned adjacent to the tab member 226. A first inner leaf spring 242 is secured to the tab member 238 and the inner cage 232, and a second inner leaf spring 244 is secured to the tab member 240 and the inner cage 232, as shown.

An outer piezoelectric bimorph actuator 248 includes a first limit stop 250, a second limit stop 252 and a piezoelectric laminate 254 where the limit stop 250 and the limit stop 254 are secured to the outer cage 218, and the piezoelectric laminate 254 is secured to the limit stop 250, as shown. An inner piezoelectric bimorph actuator 256 includes a limit stop 258, a limit stop 260, and a piezoelectric laminate 262 where the limit stop 258 and the limit stop 260 are secured to the inner cage 232, and the piezoelectric laminate 262 is secured to the limit stop 258 as shown. A retaining tab 264 is rigidly secured to the inner cage 232 and is positioned between the limit stops 250 and 252, as shown. Likewise, a retaining tab 266 is rigidly secured to the grating platform 234 and is positioned between the limit stops 258 and 260, as shown. The retaining tabs 264 and 266 operate to limit the travel of the piezoelectric laminates 254 and 262, respectively. The distance between the retaining tab 264 and the limit stop 252, and the retaining tab 266 and the limit stop 260 is small because the different positions of the grating 236 are close compared with the phase of the grating 236. The outer bimorph actuator 248 and the inner bimorph actuator 256 operate in the same manner as the piezoelectric bimorph actuator 190 discussed above.

When no voltage potential is applied to either of the piezoelectric laminates 254 and 262, the grating 254 is positioned at a first location. If a suitable voltage potential is applied to the piezoelectric laminate 262 and the piezoelectric laminate 254 has no potential applied to it, the piezoelectric laminate 262 will apply pressure against the retaining tab 266. Pressure against the retaining tab 266 will cause the platform 234 to move against the bias of the inner leaf springs 240 and 242. The platform 234 will continue to move until the retaining tab 266 contacts the limit stop 260, thus setting the position of a second location of the grating 236. If the voltage potential is removed from the piezoelectric laminate 262, the resiliency of the inner leaf springs 242 and 244 will return the grating 236 to its first location. If the voltage potential is maintained on the piezoelectric laminate 262, and a suitable voltage potential is applied to the piezoelectric laminate 254, the piezoelectric laminate 254 will apply pressure against the retaining tab 264. Pressure against the retaining tab 264 from the piezoelectric laminate 254 will cause the inner cage 232 to move against the resiliency of the outer leaf springs 228 and 230. Movement of the inner cage 232 also moves the grating platform 234. Pressure against the retaining tab 264 will cause the inner cage 232 to continue to move until the retaining tab 264 contacts the limit stop 252. This location sets the third location of the grating 236. In this manner, the MGD 216 can rapidly and accurately position the grating 236 at three locations suitable for contour mapping as discussed above.

The otoscope of the present invention can be used to establish standards of diagnosis for ear disease in published clinical trials, and other purposes by medical students, primary care physicians, general practitioners, pediatricians, internists, otolaryngologists, nurses, health care providers and other users worldwide. Practitioners can adopt the device to provide quantitative evidence for subjective diagnosis, for patient tracking and the maintenance of patient records, and to accumulate a local database on ear disease for research and clinical purposes. The ability to transmit images collected with the otoscope to remote sites at regional medical centers may be important to primary care physicians who may require expert consultation. Furthermore, the quantitative measurement of tympanic membrane compliance can be made optically by the user without referral to an audiologist for a tympanometry, thus avoiding costs for an additional test at a separate site if such equipment is not available to the user.

The otoscope of the invention is uniquely adapted to visual inspection of the external auditory meatus and the tympanic membrane. The process employed is as follows. The user first pulls the pinna of the ear gently in a caudal and superior direction to straighten the external auditory meatus. A speculum of the appropriate size for the ear to be examined is joined to the mount on the speculum and is used to determine the patency of the external auditory meatus. Illumination is provided by the light source and the speculum is inserted in the patient's meatus to view the tympanic membrane. The contour and color of the tympanic membrane and the presence of any defects therein are noted, along with the nature of light reflected off the cone-shaped area near the umbo. The image of the tympanic membrane is captured on the associated computer system of the handheld otoscope, where the image may be viewed by the physician or stored for later viewing or computer analysis. With employment of a pneumatic system, the variation in surface contour as a function of pressure in the external auditory meatus can provide an estimate of compliance of the tympanic membrane.

The presence of swellings or depressions or perforations in the tympanic membrane and changes thereto over time (hours, days, weeks, months, or years) may be analyzed (by direct comparison or by automated comparison techniques known in the art) using the invention to provide information about disease processes in the middle ear. Such analysis is useful for diagnosis of diseases of human adults, human children, and animals. Comparisons may be made between an individual image of the tympanic membrane and normative images of the tympanic membrane or normative data on the tympanic membrane, as well as between images from one individual at one or more given times, such images being stored on the computer system of the invention described above.

The surface measured by the present invention may be a biological structure or other animate or inanimate object. The object may be a naturally occurring or manufactured. The biological structure may be part of a plant or a tissue or an organ of a human or an animal. Organs of interest may be a living biological organ in situ; any of the viscera of the body; the epidermis of the body; the teeth of the mouth; or an organ of special sense, i.e., the eye, the ear, or the nose. The surface may be internal or external; any viscera or tissue of the body; one of the organs of special sense, including the conjunctiva or cornea of the eye or the pinna, external auditory meatus or tympanic membrane of the ear; one of the mucosae of the body including the mucosa of the nasopharynx, the oral mucosa, the mucosa of the larynx, the mucosa of the esophagus, the mucosa of the vagina, or the mucosa of the anus; the parietal or visceral pleura or the parietal or visceral peritoneum or any surface associated with structures in the pleural or peritoneal cavities.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of determining topography of a living structure, the method comprising the steps of:
    a) generating and directing an optical beam along a projection pathway;
    b) spatially modulating the optical beam;
    c) projecting the optical beam through a projection lens onto the structure;
    d) collecting reflected light from the structure in a detector along a detecting optical pathway;
    e) collecting reflected light from the structure by positioning viewing optics along a viewing optical pathway separate from the detecting optical pathway, wherein the reflected light impinges the viewing optics to be viewed by an operator; and
    f) generating topography of the structure from the reflected light collected by the detector.

2. The method according to claim 1 wherein the step of collecting reflected light by viewing optics is:
    simultaneous with the step of generating topography of the structure.

3. The method according to claim 1 wherein the step of collecting reflected light from the structure by viewing optics comprises generating an image of the structure by a viewing lens.

4. The method according to claim 3 further comprising the step of viewing the image of the structure generated by the viewing lens through an eyepiece of an otoscope.

5. The method according to claim 1 wherein the structure is selected from the group consisting of tissue of a body, viscera of a body, conjunctiva and cornea of an eye, pinna, external auditory meatus, mucosae of a body, and parietal and visceral pleurae.

6. The method according to claim 1 wherein the structure is a tympanic membrane of an ear.

7. The method according to claim 1 further comprising the step of generating an image of the structure.

8. The method according to claim 1 further comprising the step of recording the topography of the structure.

9. The method according to claim 1 wherein the step of collecting reflected light from the structure in a detector comprises collecting reflected light from the structure in a collecting lens and focusing the collected light onto the detector.

10. The method according to claim I wherein the steps of generating and directing an optical beam, projecting the optical beam, collecting reflected light from the structure and generating topography of the structure are all performed within an otoscope.

11. The method according to claim 1 additionally comprising the step of diagnosing a condition of the structure after the step of generating topography of the structure.

12. The method according to claim 11 wherein the step of diagnosing a condition of the structure comprises tracking changes in the structure over time.

13. The method according to claim 11 wherein the step of diagnosing a condition of the structure comprises comparing a contour of an image of the structure with a contour selected from the group consisting of normative images of a structure and images of the structure from another point in time.

14. The method according to claim 11 wherein the step of diagnosing a condition of the structure comprises detecting by processing swellings, depressions, and perforations in the structure.

15. The method according to claim 1 further comprising the step of image processing to convert data from the detector into an image of a contour map of the surface shape of the structure.

16. An apparatus for determining topography of a living structure, comprising:
    means for generating and directing an optical beam along a projection pathway;
    means for spatially modulating said optical beam;
    means for projecting the optical beam through a projection lens onto the structure;
    means for collecting reflected light from the structure in a detector along a detecting optical pathway;
    viewing optics disposed along a viewing optical pathway separate from said detecting optical pathway, wherein the reflected light impinges the viewing optics to be viewed by an operator; and
    means for generating topography of the structure from the reflected light collected by the detector.

17. The apparatus according to claim 16 wherein the collecting means comprises means for collecting reflected light simultaneous with generating topography of the structure.

18. The apparatus according to claim 16 wherein the collecting means comprises means for generating an image of the structure by a viewing lens.

19. The apparatus according to claim 18 further comprising means for viewing the image of the structure generated by the viewing lens through an eye piece of an otoscope.

20. The apparatus according to claim 16 wherein the structure is selected from the group consisting of tissue of a body, viscera of a body, conjunctiva and cornea of an eye, pinna, external auditory meatus, mucosae of a body, and parietal and visceral pleurae.

21. The apparatus according to claim 16 wherein the structure is a tympanic membrane of an ear.

22. The apparatus according to claim 16 further comprising means for generating an image of the structure.

23. The apparatus according to claim 16 further comprising means for recording the topography of the structure.

24. The apparatus according to claim 16 wherein the collecting means comprises means for collecting reflected light from the structure in a collecting lens and focusing the collected light onto the detector.

25. The apparatus according to claim 16 wherein the generating and directing means, the projecting means, the collecting means, and the generating means are all performed within an otoscope.

26. The apparatus according to claim 16 additionally comprising means for facilitating diagnosis of a condition of the structure after generating topography of the structure.

27. The apparatus according to claim 26 wherein the facilitating means comprises means for tracking changes in the structure over time.

28. The apparatus according to claim 26 wherein the facilitating means comprises means for comparing a contour of an image of the structure with a contour selected from the group consisting of normative images of a structure and images of the structure from another point in time.

29. The apparatus according to claim 26 wherein the facilitating means comprises means for detecting by processing swellings, depressions, and perforations in the structure.

30. The apparatus according to claim 16 further comprising image processing means to convert data from the detector into an image of a contour map of the surface shape of the structure.

31. A method of observing a tympanic membrane, the method comprising the steps of:
 a) generating and directing an optical beam along a projection path;
 b) projecting the optical beam through a projection lens onto the membrane;
 c) collecting reflected light from the membrane in a first collecting lens along a detecting optical pathway;
 d) directing the reflected light from the first collecting lens to a detector;
 e) generating data from the membrane from the reflected light received by the detector;
 f) sending the data from the detector to an image processing system;
 g) converting the data into an image of a topographic map of the surface of the membrane; and
 h) diagnosing a condition of the ear by tracking changes in the tympanic membrane over time;
wherein the tympanic membrane is in a living organism.

32. The method according to claim 31 further comprising the steps of:
 collecting the reflected light from the membrane in a second collecting lens along a viewing optical pathway;
 directing the reflected light from the second collecting lens to viewing optics to generate an image of the membrane; and
 viewing the image of the membrane generated by the viewing optics through a viewing lens.

33. The method according to claim 31 further comprising the step of generating a recorded image of the membrane.

34. The method according to claim 31 wherein the steps of generating and directing an optical beam, projecting the optical beam, collecting reflected light from the membrane, directing the reflected light from the collecting lens, and generating an image of the membrane, are all performed within a hand-held otoscope.

35. The method according to claim 31 further comprising the step of viewing the image of the membrane generated by the viewing optics through an eye piece of an otoscope.

36. The method according to claim 31 wherein the step of diagnosing a condition of the ear comprises comparing a contour of an image of the membrane with a contour selected from the group consisting of normative images of a tympanic membrane and images of the tympanic membrane from another point in time.

37. The method according to claim 31 wherein the step of diagnosing a condition of the ear comprises detecting by processing swellings, depressions, and perforations in the tympanic membrane.

38. An apparatus for observing a tympanic membrane, the apparatus comprising:
 means for generating and directing an optical beam along a projection path;
 means for projecting the optical beam through a projection lens onto the membrane;
 means for collecting reflected light from the membrane in a first collecting lens along a detecting optical pathway;
 means for directing the reflected light from the first collecting lens to a detector;
 means for generating data from the membrane from the reflected light received by the detector;
 means for sending the data from the detector to an image processing system;
 means for converting the data into an image of a topographic map of the surface of the membrane; and
 means for facilitating diagnosis of a condition of the ear by tracking changes in the tympanic membrane over time;
wherein the tympanic membrane comprises the tympanic membrane of a living human.

39. The apparatus according to claim 38 further comprising:
 means for collecting the reflected light from the membrane in a second collecting lens along a viewing optical pathway;
 means for directing the reflected light from the second collecting lens to viewing optics to generate an image of the membrane; and
 means for viewing the image of the membrane generated by the viewing optics through a viewing lens.

40. The apparatus according to claim 38 further comprising means for generating a recorded image of the membrane.

41. The apparatus according to claim 38 wherein the generating and directing means, the projecting means, the collecting means, the directing means, and the generating means are all performed within a hand-held otoscope.

42. The apparatus according to claim 38 further comprising means for viewing the image of the membrane generated by the viewing optics through an eye piece of an otoscope.

43. The apparatus according to claim 38 wherein the facilitating means comprises means for comparing a contour of an image of the membrane with a contour selected from the group consisting of normative images of a tympanic membrane and images of the tympanic membrane from another point in time.

44. The apparatus according to claim 38 wherein the facilitating means comprises means for detecting by processing swellings, depressions, and perforations in the tympanic membrane.

45. A moiré topographic device for characterizing a condition of an object, said device comprising:
 an illumination source, said illumination source generating an optical beam;
 means for creating a spatially modulated optical beam;
 a first gradient index lens responsive to said spatially modulated optical beam, said gradient index lens being positioned to direct said spatially modulated beam onto the object;
 a detector responsive to reflected light from the object along a detecting optical pathway, said detector providing data for characterization of the object from the reflected light; and
 viewing optics, positioned along a viewing optical pathway separate from said detecting optical pathway, wherein said reflected light impinges said viewing optics to be viewed by an operator.

46. The device according to claim 45 wherein said means for creating a spatially modulated optical beam comprises a grating, said grating modulating the optical beam to generate a modulated optical beam.

47. The device according to claim 45 wherein said first gradient index lens comprises a cylindrical gradient index lens having first and second substantially flat end surfaces, said gradient index lens having a decreasing index of refraction from a central axis to an outer surface of said lens.

48. The device according to claim 45 further comprising a second gradient index lens, said second gradient index lens being responsive to said reflected light from the object so as to direct said reflected light onto said detector.

49. The device according to claim 45 wherein said detector comprises a camera comprising an array of charge coupled devices defining individual pixels positioned to form an image of the object, wherein said camera converts intensity distributions of said reflected light beam into electrical signals to form said image of the object.

50. The device according to claim 45 further comprising a processor, said processor responsive to electrical signals from said detector indicative of said condition of the object, said processor comprising moiré topography processing systems that convert said electrical signals from said detector into a contour map of a surface shape of the object.

51. The device according to claim 50 wherein said moiré topography processing systems comprise a phase algebra means for generating contour lines of the object based on a phase of said modulation means, and a phase unwrapping means that provides a continuous contour map to eliminate ambiguities between adjacent cycles of said phase of said modulation means.

52. The device according to claim 45 further comprising a grating drive, said grating drive operable to position said grating at multiple locations during topographic determination of the object, wherein said multiple locations of said grating are within a plane of grating lines of said grating and a distance between said locations is a fraction of the period of the grating lines.

53. The device according to claim 45 wherein said device comprises an otoscope for measuring a surface shape of a tympanic membrane of an ear.

54. The device according to claim 53 wherein said otoscope comprises a body, an optical head, a speculum, and an eye piece.

55. The device according to claim 54 wherein said illumination source is positioned within said body.

56. The device according to claim 54 wherein said detector is positioned within said body.

57. The device according to claim 54 wherein said first gradient index lens is positioned within said speculum.

58. The device according to claim 54 wherein said speculum comprises a pneumatic pathway.

59. The device according to claim 45 comprising a plurality of gradient index lenses disposed therein to mediate a plurality of optical pathways.

60. The device according to claim 45 wherein said illumination source comprises a non-coherent, white light source.

61. The device according to claim 45 wherein said object is selected from the group consisting of natural and manufactured objects.

62. The device according to claim 45 wherein said object is selected from the group consisting of living biological tissues in situ, viscera of a body, epidermis of a body, teeth of a mouth, an eye, a nose, mucosae of a body, and parietal and visceral pleurae.

63. A method of characterizing a condition of an object, the method comprising the steps of:
   a) generating an optical beam from an illumination source;
   b) spatially modulating the optical beam;
   c) projecting the modulated optical beam onto the object by a first gradient index lens; and
   d) employing a camera comprising an array of charge coupled devices defining individual pixels positioned to form an image of the object, wherein the camera converts intensity distributions of the reflected light beam into electrical signals to form the image of the object, thereby providing data for characterization of the object from reflected light via a detector responsive to the reflected light from the object along a detecting optical pathway.

64. The method according to claim 63 wherein the spatially modulating step comprises employing a grating to generate a modulated optical beam.

65. The method according to claim 63 wherein the projecting step comprises employing a cylindrical gradient index lens having first and second substantially flat end surfaces, the gradient index lens having a decreasing index of refraction from a central axis to an outer surface of the lens.

66. The method according to claim 63 further comprising employing a second gradient index lens, the second gradient index lens being responsive to the reflected light from the object so as to direct the reflected light onto the detector.

67. The method according to claim 63 further comprising employing a processor, the processor responsive to electrical signals from the detector indicative of the condition of the object, the processor comprising moiré topography processing systems that convert the electrical signals from the detector into a contour map of a surface shape of the object.

68. The method according to claim 67 wherein the employing step comprises generating by phase algebra contour lines of the object based on a phase of the modulated optical beam, unwrapping a phase to provide a continuous contour map to eliminate ambiguities between adjacent cycles of the phase of the modulated optical beam.

69. The method according to claim 63 further comprising employing a grating drive, the grating drive operable to position the grating at multiple locations during determination of topography of the object, wherein the multiple locations of the grating are within a plane of grating lines of the grating and a distance between the locations is a fraction of the period of the grating lines.

70. The method according to claim 63 further comprising employing viewing optics, wherein the reflected light impinges the viewing optics to be viewed by an operator.

71. The method according to claim 70 wherein the employing step comprises positioning viewing optics along a viewing optical pathway separate from the detecting optical pathway.

72. The method according to claim 63 wherein the method comprises measuring a surface shape of a tympanic membrane of an ear with an otoscope.

73. The method according to claim 72 wherein the measuring step comprises employing an otoscope comprising a body, an optical head, a speculum, and an eyepiece.

74. The method according to claim 73 wherein the measuring step comprises positioning an illumination source within the body.

75. The method according to claim 73 wherein the measuring step comprising positioning the detector within the body.

76. The method according to claim 73 wherein the measuring step comprises positioning the first gradient index lens within the speculum.

77. The method according to claim 73 wherein the measuring step comprises positioning a pneumatic pathway within the speculum.

78. The method according to claim 63 additionally comprising employing multiple gradient index lenses disposed to mediate multiple optical pathways.

79. The method according to claim 63 wherein the generating step comprises employing an illumination source comprising a non-coherent, white light source.

80. The method according to claim 63 additionally comprising the step of selecting the object from the group consisting of natural and manufactured objects.

81. The method according to claim 63 additionally comprising the step of selecting the object from the group consisting of living biological tissues in situ, viscera of a body, epidermis of a body, teeth of a mouth, an eye, a nose, mucosae of a body, and parietal and visceral pleurae.

82. A device for determining contour of a living structure, said device comprising:
   an illumination source, said illumination source generating and transmitting an optical beam along a projection path to impinge the structure;
   a grating positioned along said projection path and being responsive to said optical beam, said grating creating a modulated optical beam that produces light and dark fringe patterns on the structure;
   a detector positioned along a detection path, said detector responsive to a reflected light beam from the structure and providing electrical signals of intensity variations of said reflected beam, said detector comprising a camera comprising an array of charge coupled devices defining individual pixels to form said image of the structure, said camera converting intensity distributions of said reflected light beam into electrical signals to form said image of the structure; and
   a processor responsive to electrical signals from said detector indicative of an image of the structure, said processor including moiré topography processing means that convert said electrical signals from said detector into a contour map of a surface shape of the structure.

83. The device according to claim 82 further comprising viewing optics positioned along a viewing path, said viewing optics being responsive to said reflected light beam from the structure so as to provide viewing of the structure by an operator.

84. The device according to claim 82 further comprising a first gradient index lens positioned along said projection path, said first gradient index lens being responsive to said modulated optical beam from said grating so as to project said fringe pattern onto the living structure.

85. The device according to claim 84 further comprising a second gradient index lens, said second gradient index lens being positioned along said detection path so as to project said reflected light beam onto said detector.

86. The device according to claim 85 further comprising a third gradient index lens, said third gradient index lens being positioned along said viewing path so as to project said reflected light beam onto said viewing optics.

87. The device according to claim 84 wherein said first gradient index lens comprises a cylindrical gradient index lens having first and second substantially flat end surfaces and a decreasing index of refraction from a central axis to an outer surface of said cylindrical gradient index lens.

88. The device according to claim 82 further comprising a grating drive, said grating drive operable to position said grating at multiple locations during a contour measurement of the structure, wherein said multiple locations of said grating are within a plane of grating lines of said grating and the distance between said locations is a fraction of the period of the grating pattern projected on the structure.

89. The device according to claim 82 wherein said device comprises an otoscope for measuring a surface shape of a tympanic membrane of an ear, said otoscope comprising a body, an optical head, a speculum, and an eye piece.

90. The device according to claim 89 wherein said illumination source, is positioned within said body.

91. The device according to claim 89 wherein said grating is positioned within said body.

92. The device according to claim 89 wherein said detector is positioned within said body.

93. The device according to claim 89 wherein said viewing optics is positioned within said optical head.

94. The device according to claim 82 wherein said processor comprises a data storage or transmission system selected from the group consisting of floppy disks, hard drive storage devices, hard copy printers, video displays, and transmitters.

95. The device according to claim 82 wherein the structure is selected from the group consisting of tissue of a body, viscera of a body, conjunctiva and cornea of an eye, pinna, external auditory meatus, tympanic membrane of an ear, mucosae of a body, and parietal and visceral pleurae.

96. A method for determining contour of a living structure, the method comprising:
   a) generating and transmitting an optical beam along a projection path to impinge the structure, via an illumination source;
   b) creating a modulated optical beam that produces light and dark fringe patterns on the structure, via a grating positioned along the projection path and being responsive to the optical beam;
   c) providing electrical signals of intensity variations of a reflected beam, via a detector positioned along a detection path, the detector responsive to the reflected light beam from the structure, by providing a camera comprising an array of charge coupled devices defining individual pixels to form the image of the structure, the camera converting intensity distributions of the reflected light beam into electrical signals to form the image of the structure; and
   d) employing a processor responsive to electrical signals from the detector indicative of an image of the structure, the processor including moiré topography processing means that convert the electrical signals from the detector into a contour map of a surface shape of the structure.

97. The method according to claim 96 further comprising positioning viewing optics along a viewing path, the viewing optics being responsive to the reflected light beam from the structure so as to provide viewing of the structure by an operator.

98. The method according to claim 96 further comprising positioning a first gradient index lens along the projection path, the first gradient index lens being responsive to the modulated optical beam from the grating so as to project the fringe pattern onto the living structure.

99. The method according to claim 98 further comprising positioning a second gradient index lens along the detection path so as to project the reflected light beam onto the detector.

100. The method according to claim 99 further comprising positioning a third gradient index lens along the viewing path so as to project the reflected light beam onto the viewing optics.

101. The method according to claim 98 wherein the positioning step comprises positioning a first gradient index lens comprising a cylindrical gradient index lens having first and second substantially flat end surfaces and a decreasing index of refraction from a central axis to an outer surface of the cylindrical gradient index lens.

102. The method according to claim 96 further comprising the step of employing a grating drive, the grating drive operable to position the grating at multiple locations during a contour measurement of the structure, wherein the multiple locations of the grating are within a plane of grating lines of the grating and the distance between the locations is a fraction of the period of the grating pattern projected on the structure.

103. The method according to claim 96 wherein the method comprises measuring via an otoscope a surface shape of a tympanic membrane of an ear, the otoscope comprising a body, an optical head, a speculum, and an eye piece.

104. The method according to claim 103 wherein the generating and transmitting step comprises employing an illumination source positioned within the body.

105. The method according to claim 103 additionally comprising the step of positioning the grating within the body.

106. The method according to claim 103 additionally comprising the step of positioning the detector within the body.

107. The method according to claim 103 additionally comprising the step of positioning the viewing optics within the optical head.

108. The method according to claim 96 wherein the employing step comprises employing a data storage or transmission system selected from the group consisting of floppy disks, hard drive storage methods, hard copy printers, video displays, and transmitters.

109. The method according to claim 96 additionally comprising the step of selecting the structure from the group consisting of tissue of a body, viscera of a body, conjunctiva and cornea of an eye, pinna, external auditory meatus, tympanic membrane of an ear, mucosae of a body, and parietal and visceral pleurae.

* * * * *